United States Patent [19]

Schaeffer

[11] Patent Number: 4,528,180

[45] Date of Patent: Jul. 9, 1985

[54] DENTAL PREPARATION, ARTICLE AND METHOD FOR STORAGE AND DELIVERY THEREOF

[76] Inventor: Hans A. Schaeffer, 14 Pallant Ave., Linden, N.J. 07036

[21] Appl. No.: 471,188

[22] Filed: Mar. 1, 1983

[51] Int. Cl.³ .................. B65D 35/22; A61K 7/16; A61K 7/18; A61K 7/20

[52] U.S. Cl. .................. 424/52; 222/92; 222/94; 222/192; 424/53; 424/130

[58] Field of Search .................. 424/53, 130, 44; 222/92, 94, 192

[56] References Cited

U.S. PATENT DOCUMENTS

| | | | |
|---|---|---|---|
| 636,986 | 11/1899 | Heinen | 424/130 |
| 959,605 | 5/1910 | Queisser | 424/130 |
| 1,535,529 | 4/1925 | Hopkins | 424/53 |
| 1,566,218 | 12/1925 | Leland | 424/49 |
| 2,035,267 | 3/1936 | Fleischman | 424/53 |
| 2,054,742 | 9/1936 | Elbel | 424/53 |
| 2,789,731 | 4/1957 | Marraffino | 222/129 |
| 3,175,731 | 3/1965 | Ellman | 424/52 |
| 3,499,844 | 3/1970 | Kibbel et al. | 252/316 |
| 3,577,521 | 5/1971 | Scheller et al. | 424/55 |
| 3,639,574 | 2/1972 | Schmolka | 424/130 |
| 3,874,558 | 4/1975 | Rockefeller | 222/92 |
| 3,881,529 | 5/1975 | Mannara | 141/100 |
| 3,907,991 | 9/1975 | Accetta | 424/130 |
| 3,937,321 | 2/1976 | Delaney et al. | 206/84 |
| 4,060,179 | 11/1977 | McGhie | 222/92 |
| 4,098,435 | 7/1978 | Weyn | 222/94 |
| 4,130,501 | 12/1978 | Lutz et al. | 252/186 |
| 4,211,341 | 7/1980 | Weyn | 222/94 |
| 4,223,003 | 9/1980 | Scheller | 424/49 |
| 4,330,531 | 5/1982 | Alliger | 424/53 |
| 4,487,757 | 12/1984 | Kiozpeoplou | 424/7.1 |

FOREIGN PATENT DOCUMENTS

| | | |
|---|---|---|
| 1492660 | 11/1977 | United Kingdom . |
| 1565672 | 4/1980 | United Kingdom . |
| 2112642A | 7/1983 | United Kingdom . |

OTHER PUBLICATIONS

Goupil, Chem. Abstracts, 87#11477h, (1977) of Ger. Offen. No. 2,643,411, Apr. 7, 1977, (14 pages), (Compartmental Peroxide and Acid Toothpaste).

*Primary Examiner*—Shep K. Rose
*Attorney, Agent, or Firm*—Darby & Darby

[57] ABSTRACT

The invention is directed to a combination of a collapsible tube article having flexible side walls and a composition consisting of a gel component and a paste component and contained in said article, said combination being suitable for use in combatting gum disease, said article comprising:

(a) a first compartment containing said gel, said gel comprising (i) 1–10% by volume of hydrogen peroxide, (ii) 0.05–1.2% by volume of a water dispersible copolymer of acrylic acid cross-linked with polyallyl sucrose; (iii) 0.1–1.5% by volume of a non-ionic cellulose gum stabilizer (iv) purified water and (iv) a neutralizing agent selected from the group consisting of sodium hydroxide, potassium hydroxide, triethanolamine, diisopropylamine and ammonia in an amount sufficient to raise the pH of said gel to within about 3–6 said first compartment having an orifice for dispensing controlled amounts of said gel upon squeezing of said flexible sidewalls;

(b) a second compartment containing said paste, said paste comprising (i) 10–50% by weight of sodium bicarbonate; (ii) 1–6% by weight of a salt selected from the group consisting of NaCl and $MgSO_4$; (iii) 1–3% by weight of a thickener-stabilizer selected from the group consisting of cellulose gum magnesium aluminum silicate, and mixtures thereof; (iv) 5–30% by weight of a humectant selected from the group consisting of glycerin, sorbitol, polyethylene glycol and polypropylene glycol, (v) purified water and (vi) 1–40% by weight of a cleaning-polishing agent selected from the group consisting of $CaSO_4$, $Ca_3(PO_4)_2$ and hydrated aluminum oxide, and (viii) 0.1–2.5% by weight of sodium lauryl sulfate.

6 Claims, 4 Drawing Figures

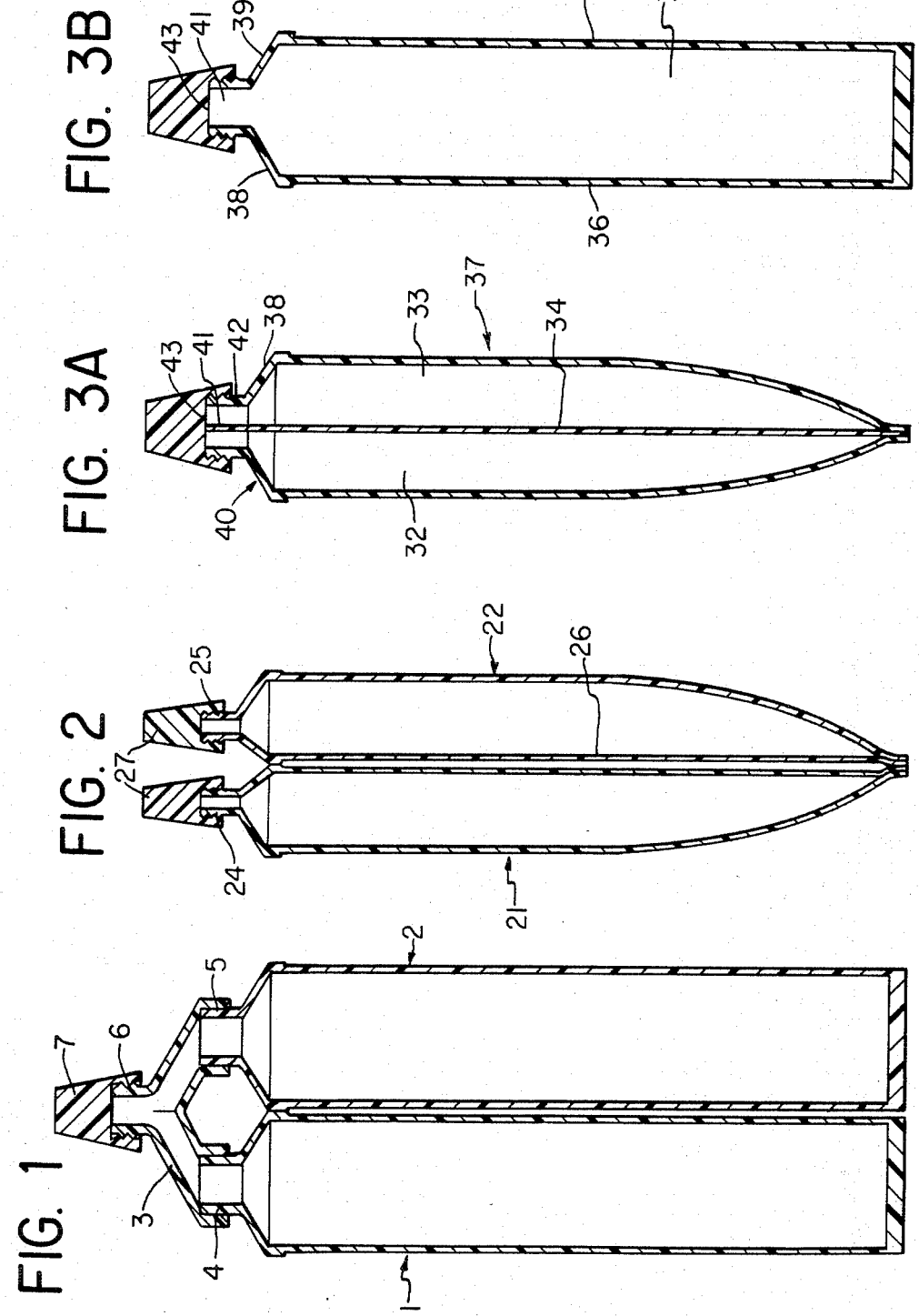

DENTAL PREPARATION, ARTICLE AND METHOD FOR STORAGE AND DELIVERY THEREOF

This invention relates to a dental preparation useful in the treatment of gum disease, to a method of storing and delivering such preparation to a use point and to an article for the storage and delivery of such preparation.

It has long been recognized that the combination of hydrogen peroxide solution with sodium bicarbonate and table salt has an excellent curative and preventive effect on gum disease caused by bacterial infection. Dr. Paul H. Keyes has advocated use of this combination to the dental profession and to the public at large based on his work of more than 25 years on the subject, which has shown that upon daily and diligent topical application of these materials, gum disease may be effectively controlled. On the basis of his recommendations, many dentists urge their patients to use the Keyes procedure (substantially as described e.g. in S. Elder: "An Alternative To Gum Surgery" Modern Maturity, August-September 1980 pp. 31-32).

Dr. Keyes advocates that a quantity of solid sodium bicarbonate be placed in one hand, and that the toothbrush, held in the other hand, be dipped into a hydrogen peroxide—table salt solution and then transferred to the bicarbonate and applied to the teeth and gums. Upon contact with the gums, the hydrogen peroxide is exposed to the enzyme catalase, which is always present in the buccal cavity, and is attacked thereby resulting in the release of active oxygen. The combination of the active oxygen and the sodium bicarbonate together with table salt destroys the bacteria responsible for gum desease. Unfortunately, hydrogen peroxide and sodium bicarbonate may not be premixed, as they immediately react and are thereby rendered ineffective against gum desease. In addition, hydrogen peroxide is unstable and therefore difficult to store for prolonged periods of time. Finally, mere dipping of the toothbrush in a hydrogen peroxide solution does not insure delivery of a sufficient amount of hydrogen peroxide to the teeth and gums. These factors are responsible for the fact that use of the Keyes procedure is extremely awkward, inconvenient and messy. Another disadvantage stems from the fact that, the mixture of hydrogen peroxide and sodium bicarbonate has a very unpleasant taste. For these reasons, patients have shown extreme reluctance to follow this procedure, especially on a daily basis, as would be required for effective gum desease control. As a result, the benefits which the Keyes procedure affords have largely been left unrealized.

Accordingly, it is an object of this invention to eliminate the above disadvantages associated with use of the Keyes procedure by providing a dental preparation incorporating the active constituents of the Keyes procedure that has pleasant taste and is neat and convenient to use, and a method for using such preparation that permits contact between hydrogen peroxide and sodium bicarbonate only shortly before use and, therefore, assures maximum effectiveness against gum disease.

It is another object of the present invention to provide a dental preparation incorporating the active constituents of the Keyes method and a method for using such preparation that permits a sufficient, consistent and reproducible amount of hydrogen peroxide to be delivered to the use point.

It is yet another object of this invention to provide an article for the storage and delivery of this improved dental preparation which makes its use neat and convenient and which prevents contact between hydrogen peroxide and sodium bicarbonate prior to application.

In accordance with the present invention, hydrogen or urea peroxide is dissolved in an aqueous nontoxic gel for use in combination with a separately stored but substantially simultaneously dispensed paste containing sodium bicarbonate, table salt, and, preferably, additional cleansing and polishing agents as well as an effective concentration of flavoring substances. Each of the gel and paste are loaded either into separate collapsible containers which are connected by means of a common orifice (as in FIG. 1), or which have substantially adjacent orifices (as in FIG. 2), or in separate compartments of a single container (as in FIG. 3).

Upon substantially simultaneous squeezing of the containers, in much the same way as common toothpaste tubes, controlled quantities of the gel and paste can be simultaneously released onto the toothbrush and immediately applied to the teeth and gums. Control of the $H_2O_2$, NaCl and $NaHCO_3$ quantities delivered may be thus effected by specification of the opening of the orifice and the active ingredient concentration in each tube. As described above, when the brush is applied to teeth and gums, immediate mixing of the products takes place followed by the rapid evolution of active oxygen and carbon dioxide. At the same time, the effervescence accompanying release of active oxygen activates the flavor contained in the bicarbonate paste and produces a lasting highly refreshing taste in the mouth which is unlike any other flavor provided by existing toothpastes or gels. Another advantage afforded by the present invention, as compared with the Keyes procedure, is that a greater and more consistent amount of hydrogen peroxide is delivered to the use point.

Gelling agents suitable for use in preparation of the $H_2O_2$ gel in accordance with this invention should be nontoxic and neutral to the hydrogen peroxide to assure its stability. In addition, they should be preferably sensitive to external electrolytes, such as those contained in the sodium bicarbonate paste, in order to make hydrogen peroxide immediately available to the oral tissues. A gelling agent suitable for use with the present invention is a copolymer of acrylic acid cross-linked with polyallyl sucrose, as described in U.S. Pat. No. 2,798,053 issued on July 2, 1957 and assigned to B. F. Goodrich Inc. Other gelling agents resulting in stable hydrogen peroxide gels suitable for use in the present invention include those described in British Pat. No. 827,331, i.e., organic polymeric acid colloids including polyuronic acids, carboxypolymethylene compounds and polyester resins containing three carboxyl groups, such as partially hydrolized polyacrylates or polymethacrylates and copolymers thereof; and those described in U.S. Pat. No. 3,639,574 issued on Feb. 1, 1972 to Schmolka, i.e., polyoxyethylene polyoxypropylene block copolymers, which, according to Schmolka, may be used in the preparation of stable, firm hydrogen peroxide gels. Preferred are water dispersible copolymers of acrylic acid cross-linked with about 0.75 to about 1.5% of polyallyl sucrose and neutralized with triethanolamine, NaOH or another alkalizing agent, as taught in U.S. Pat. No. 3,499,844[1] issued on Mar. 10, 1970 to Kibbel et al. For purposes of the present invention, Kibbel's acrylic copolymer may be preferably combined with an anionic or non-ionic surfactant, such as disclosed in U.S. Pat. No. 4,130,501[1] issued on Dec. 19, 1978 to Lutz et al. Such surfactants are not essential for the formation of a stable hydrogen peroxide gel in accordance with this invention, but may be added to facilitate distribution and rapid penetration of the active oxygen throughout the area to be treated. The most preferred gelling agent for the purposes of the present invention is that described by Kibbel, supra, modified by the addition of a suitable amount of non-ionic cellulose gum such as hydroxyethyl or hydroxypropyl-cellulose or hydroxypropyl methylcellulose in order to improve the physical stability of the gel, especially when subjecting it to stress such as that resulting from squeezing of the collapsible tubes. In addition, a small quantity of a surfactant may be added in order to enhance the dispersibility of the gel when mixed with a sodium bicarbonate paste.

[1] The disclosures of these patents are incorporated herein by reference.

The hydrogen peroxide gel may then contain the following ingredients in the following amounts —$H_2O_2$: about 1.0–10.0% and preferably about 3.0–6.5%; Acrylic acid copolymer: about 0.05–1.20% and, preferably, about 0.3–0.8%; nonionic cellulose gum: about 0.1–1.5% and, preferably, about 0.3–0.8%; neutralizing agent (triethanolamine, diisopropanolamine, NaOH, KOH): an amount sufficient to raise the gel pH to about 3.0–6.0. The balance is purified (distilled or deionized) water.

The sodium bicarbonate paste contains sodium bicarbonate, sodium chloride, purified (distilled or deionized) water and a thickener/stabilizer such as cellulose gum and magnesium-aluminum silicate, as essential ingredients. In order to disperse the "chalky" taste imparted mostly by the bicarbonate, a bodying agent is added, such a sorbitol, glycerin or a glycol. In addition, if the paste, in combination with the gel, is to displace toothpaste completely, cleansing agents, such as calcium sulfate, calcium phosphate and hydrated aluminum oxide, as well as a foaming agent such as sodium lauryl sulfate (which also enhances the peroxide-bicarbonate-salt action) may be added. Flavoring agents, such as sodium saccharin, or other artificial sweeteners, peppermint or spearmint or other flavors are preferably added to further curb the unpleasant taste. Finally, methyl and/or propyl paraben are preferably added as preservatives. Use of a coloring agent is optional.

The constituents and quantities for the bicarbonate paste are as follows: sodium bicarbonate: about 10–50% and preferably 20–40%; polyol: about 5–30% and preferably, 15–25%; cellulose gum: about 1–3% and preferably 1.2–1.8%; sodium chloride: about 1–6% and preferably about 2–4%; polishing agent/cleanser: about 1–40%, preferably about 1.5–30%; foaming agent: about 0.1–2.5% and preferably about 0.2–0.5%; flavoring agent(s): to taste, less than about 1%; preservatives: about 0.1–0.5%. The balance is purified water. The paste and the gel are preferably used in substantially equal proportions, by volume.

The gel and paste combination may be simultaneously dispensed from separate collapsible tubes preferably made of plastic, or a plastic/metal laminate (to avoid reaction with $H_2O_2$), such as tubes 1 and 2 shown in FIG. 1. The tubes are fitted with a Y-shaped conduit 3 which provides them with a common orifice 6. Conduit 3 may also be made of plastic (preferably by injection molding) and is preferably detachably but snugly attached to mouths 4,5 of tubes 1,2 so that it may be removed for cleaning. For additional convenience and in order to ensure dispensation of substantially equal amounts of the gel and paste, the tubes themselves may be held together, e.g., by banding or cementing, along corresponding dorsal sides, shown in FIG. 1, or, preferably, along corresponding ventral sides (see, e.g., FIG. 3A).

Alternatively, the two tubes may be constructed to have a common (preferably flat) sidewall portion 26 as shown in FIG. 2. In the latter case, the Y-shaped conduit may be unnecessary, if the mouths 24,25 of tubes 21,22 are sufficiently close so that sufficient quantities of the gel and paste may be simultaneously dispensed directly on the toothbrush. Conventional toothpaste or medicament tubes may be thus used after one of their side walls and the corresponding portion of their head structure are permanently deformed (e.g. by application of pressure) to a substantially flat surface.

A third alternative packaging method involves loading each of the gel and paste into separate compartments of the same collapsible tube, joined by a common orifice, as shown in FIG. 3. Composite tube 31 has compartments 32, 33 separated by divider 34 which is firmly attached along substantially diametrically opposed portions 35,36 of the sidewall 37, and corresponding portions 38,39 of head structure 40. Divider 34 may be glued or welded to sidewall 37 and head structure 40 of tube 31 during manufacture of the latter. Divider 34 is preferably provided with protruding portion 41, which extends into the mouth 42 of tube 31 until its edge is substantially flush with rim 43 of mouth 42. Thus, divider 34 forms with sidewall 37 two separate compartments 32,33 of substantially the same volume for storage of the gel and paste, respectively.

Tubes, such as those suitable for use in accordance with the present invention are usually extruded around a cylindrical mandrel, cut into tube segments of suitable length, fitted with head structures and then filled from the bottom and pressed and/or welded closed, substantially as described in, e.g., U.S. Pat. No. 4,060,179 issued on Nov. 29, 1977 to McGhie, the disclosure of which is incorporated herein by reference.

The invention is further illustrated by the following specific examples which are designed merely to illustrate the present invention and not to limit its scope.

In these examples, a hydrogen peroxide gel containing 3–6.5% hydrogen peroxide by weight, useful for simultaneous administration with a sodium bicarbonate paste is prepared as follows:

EXAMPLE 1

Ingredients

Hydrogen peroxide, 35% aqueous solution (5% $H_2O_2$ in final gel): 14.3 parts

Purified water: 84.45

Copolymer of acrylic acid crosslinked with 1% by weight of polyallyl sucrose having 5.8 allyl groups per molecule (CARBOPOL 934 made by B. F. Goodrich Chemical Co., Akron, Ohio): 0.5

Hydroxyethyl cellulose: 0.5

Triethanolamine: 0.25

The gel is prepared by combining the hydrogen peroxide solution with the purified water, followed by the gradual addition of CARBOPOL 934. Upon thorough dispersion of the copolymer hydroxyethyl cellulose is slowly added and dissolved. Finally, triethanolamine is added, forming a clear, homogeneous, stable and viscous gel having a pH of 3.4.

EXAMPLE 2

Ingredients

Hydrogen peroxide, 35% aq. solution (3.5% $H_2O_2$ in final gel): 10.0 parts
Distilled or deionized water: 88.9
Acrylic acid copolymer CARBOPOL 940 (Goodrich): 0.6
Hydroxyethylcellulose: 0.5
Sodium hydroxide, 10% solution: q.s. pH 3.8–4.0
Preparation: same as that of Example 1.

EXAMPLE 3

Ingredients

Hydrogen peroxide, 35% (3.5% $H_2O_2$ in final gel): 10.0 parts
Distilled or deionized water: 89.0
Acrylic acid copolymer—CARBOPOL 941 (Goodrich): 0.7
Hydroxypropylcellulose: 0.3
Sodium hydroxide, 10% solution: q.s. pH 3.8–4.0
Preparation: same as that of Example 1.

EXAMPLE 4

Ingredients

Hydrogen peroxide, 35% (4.0% $H_2O_2$ in final gel): 11.5 parts
Distilled or deionized water: 86.65
Acrylic acid copolymer—CARBOPOL 934 (Goodrich): 0.75
Sodium laurylsulfate, dentifrice grade: 0.50
Hydroxypropylcellulose: 0.6
Sodium hydroxide, 10% solution: q.s. pH 3.5–4.5
Preparation:

The hydrogen peroxide solution is combined with the distilled or deionized water. Sodium laurylsulfate is added under constant agitation and dissolved. Gradually, CARBOPOL 934 is added and dispersed. Hydroxypropylcellulose is added in increments and dissolved. When the mixture is homogeneous, sodium hydroxide is added slowly to the desired pH level and viscosity.

EXAMPLE 5

Ingredients

Hydrogen peroxide, 35% (6.0% $H_2O_2$ in final gel): 17.14 parts
Distilled or deionized water: 81.76
Acrylic acid copolymer—CARBOPOL 940 (Goodrich): 0.70
Hydroxyethylcellulose: 0.40
Sodium hydroxide, 10% solution: q.s. pH 3.5–4.0
Preparation: same as that of Example 1.

EXAMPLE 6

Ingredients

Hydrogen peroxide, 35% (3.0% $H_2O_2$ in final gel): 8.58 parts
Distilled or deionized water: 89.22
Acrylic acid copolymer—CARBOPOL 934 (Goodrich): 0.70
Hydroxypropyl methylcellulose: 0.65
Nonionic surfactant PLURONIC F 127 (BASF Corp., New Jersey): 0.85
Sodium hydroxide, 10% solution: q.s. pH 3.5–4.5
Preparation: same as that of Example 4.

EXAMPLE 7

The sodium bicarbonate paste is prepared as follows:

Ingredients

Deionized water: 31.94 parts
Sorbitol 70% solution, USP: 20.0
Cellulose gum—CMC 7MF (Hercules): 1.44
Sodium saccharin: 0.20
Magnesium aluminum silicate—VEEGUM F (made by R. T. Vanderbilt Co., Inc., Norwalk, Conn.): 1.17
Sodium bicarbonate, fine powder: 40.00
Sodium chloride: 4.00
Sodium lauryl sulfate—dentifrice grade: 0.30
Peppermint/Spearmint Flavor: 0.75
Methyl paraben, USP: 0.15
Propyl paraben, USP: 0.05
Procedure:

Glycerin and propylene glycol are combined in a first container with agitation. Cellulose gum is added and dispersed thoroughly throughout the mixture. Saccharin, methylparaben and propylparaben are added in a separate container and heated to dissolve. VEEGUM is added and the mixture is agitated until uniform. The contents of the first container are slowly added to the second container and the final mixture is agitated thoroughly until uniform. Flavoring agent, sodium lauryl sulfate and coloring (if desired) are added and the paste is agitated at moderate speed until uniform. Further homogeneity may be obtained by milling, if necessary.

EXAMPLE 8

Ingredients

Deionized water: 33.43 parts
Glycerin: 10.00
Propylene glycol: 10.0
Cellulose gum—CMC 7MF (Hercules): 1.45
Sodium saccharin: 0.20
Magnesium aluminum silicate—VEEGUM F: 1.17
Sodium bicarbonate, fine powder: 25.00
Dicalcium phosphate dihydrate: 13.50
Dicalcium phosphate, anhydrous: 1.50
Sodium chloride: 2.50
Sodium lauryl sulfate, dentifrice grade: 0.30
Methylparaben, USP: 0.15
Propylparaben, USP: 0.05
Peppermint/Spearmint Flavor: 0.75
FD & C Blue No. 1, 0.1% solution: q.s
DS & C Yellow No. 6, 0.1% solution: q.s.
Procedure: Same as that of Example 8.

EXAMPLE 9

Paste containing fluoride:

Ingredients

Deionized water: 33.51
Sorbitol, 70% solution: 20.00
Sodium saccharin: 0.20
Cellulose gum CMC 7MF (Hercules): 1.54
Magnesium aluminum silicate—VEEGUM F: 1.17
Sodium fluoride: 0.33
Methyl paraben, USP: 0.15
Propyl paraben, USP: 0.05
Calcium sulfate: 10.00
Sodium bicarbonate: 25.00
Sodium chloride: 2.00

Hydrated aluminum oxide: 5.00
Peppermint/Spearmint Flavor: 0.75
Sodium lauryl sulfate: 0.30
Procedure: Same as that of Example 8.

EXAMPLE 10

Ingredients

Urea peroxide, 35% $H_2O_2$ equivalent (5% $H_2O_2$ in final gel): 14.3 parts
Purified water: 84.45
Copolymer of acrylic acid crosslinked with 1% by weight of polyallyl sucrose having 5.8 allyl groups per molecule (CARBOPOL 934 made by B. F. Goodrich Chemical Co., Akron, Ohio): 0.5
Hydroxyethyl cellulose: 0.5
Triethanolamine: 0.25

The gel is prepared by combining the hydrogen peroxide solution with the purified water, followed by the gradual addition of CARBOPOL 934. Upon thorough dispersion of the copolymer hydroxyethyl cellulose is slowly added and dissolved. Finally, triethanolamine is added, forming a clear, homogeneous, stable and viscous gel having a pH of 3.4.

What is claimed is:

1. A combination of a collapsible tube article having flexible side walls and a composition consisting of a gel component and a paste component and contained in said article, said combination being suitable for use in combatting gum disease, said article comprising:
   (a) a first compartment containing said gel, said gel comprising (i) 1–10% by volume of hydrogen peroxide, (ii) 0.05–1.2% by volume of a water dispersible copolymer of acrylic acid cross-linked with polyallyl sucrose; (iii) 0.1–1.5% by volume of a non-ionic cellulose gum stabilizer (iv) purified water and (iv) a neutralizing agent selected from the group consisting of sodium hydroxide, potassium hydroxide, triethanolamine, diisopropylamine and ammonia in an amount sufficient to raise the pH of said gel to within about 3–6 such that the gel liquifies immediately upon contact with a mildly alkaline environment containing a strong electrolyte, thereby causing the release of bactericidally effective amounts of nascent oxygen; said gel having sufficient viscosity to support itself on the bristles of a toothbrush and sufficient fluidity to be dispensed from said flexible sidewall tube article upon squeezing; said first compartment having an orifice for dispensing controlled amounts of said gel upon squeezing of said flexible sidewalls;
   (b) a second compartment containing said paste, said paste comprising (i) 10–50% by weight of sodium bicarbonate; (ii) 1–6% by weight of a salt selected from the group consisting of NaCl and $MgSO_4$; (iii) 1–3% by weight of a thickener-stabilizer selected from the group consisting of cellulose gum magnesium aluminum silicate, and mixtures thereof; (iv) 5–30% by weight of a humectant selected from the group consisting of glycerin, sorbitol, polyethylene glycol and polypropylene glycol, (v) purified water and (vi) 1–40% by weight of a cleansing-polishing agent selected from the group consisting of $CaSO_4$, $Ca_3(PO_4)_2$ and hydrated aluminum oxide, and (viii) 0.1–2.5% by weight of sodium lauryl sulfate; said paste having sufficient viscocity to support itself on the bristles of a toothbrush and sufficient fluidity to be dispensed from said flexible sidewall tube by squeezing, said second compartment having an orifice for dispensing controlled amounts of said paste upon squeezing of said flexible sidewalls substantially simultaneously with the dispensation of said gel in substantially equal amounts; said first compartment orifice and said second compartment orifice being adapted to dispense said gel and said paste respectively at the same use point, said first and second compartments having a common wall portion and said orifices being substantially adjacent; said article affording the following advantages over the use of an $H_2O_2$, $NaHCO_3$ and NaCl combination formed by dipping a toothbrush in a supply of $H_2O_2$ followed by dipping said toothbrush in a paste consisting of $NaHO_3$, NaCl and $H_2O_2$:
   (i) ready availability of premeasured bactericidally effective amounts of active $H_2O_2$ and $NaHCO_3$ sufficient to combat gum disease and effective against bacterial plaque;
   (ii) more vigorous release of said $O_2$ due to the presence of said gel having a pH of about 3–6 on one hand and the presence of $NaHCO_3$, which is alkanine, and NaCl, which is a strong electrolyte, on the other hand;
   (iii) improved penetration into gum tissues of nascent oxygen $NaHCO_3$ and NaCl and more intimate contact with tooth and gum surfaces; and
   (iv) substantially smoother texture and a more palatable and pleasant taste.

2. The article of claim 1 wherein said first and second compartments are substantially equivolumetric parts of a single collapsible tube having one orifice, divided into said compartments by a divider, said divider extending into said orifice.

3. The article of claim 1 wherein said gel component comprises 3–6.5% $H_2O_2$, 0.3–0.8% acrylic acid copolymer and 0.3–0.8% nonionic cellulose gum stabilizer and wherein said paste component comprises 20–40% sodium bicarbonate, 2–4% NaCl, 1.2–1.8% of said thickener-stabilizer, 15–25% of said humectant, and wherein said paste component further comprises: from zero to about 1% by weight of a flavoring agent selected from the group consisting of artificial sweeteners, spearmint flavor, peppermint flavor, cinnamon flavor, citrus flavor and mixtures thereof; and 0.1–0.5% by weight of a member of the group consisting of methylparaben, propyl paraben and mixtures thereof.

4. The article of claim 3, wherein said gel cellulose gum stabilizer is hydroxypropylcellulose, said neutralizing agent is sodium hydroxide, said paste thickener-stabilizer is a mixture of cellulose gum and magnesium aluminum silicate, said humectant is sorbitol and said cleansing-polishing agent is calcium sulfate.

5. A method of combating gum disease comprising substantially simultaneously dispensing the gel and paste of the article according to claim 1 by squeezing the flexible sidewalls of said article.

6. The composition of claim 1, wherein said paste component also contains a fluoride compound effective against caries, said composition being suitable as a toothpaste substitute also effective against gum disease.

* * * * *